United States Patent
Cheong et al.

(10) Patent No.: US 7,214,955 B2
(45) Date of Patent: May 8, 2007

(54) MEDIA RECOGNITION USING A SINGLE LIGHT DETECTOR

(75) Inventors: Jiin Cheang Cheong, Penang (MY); Boon Keat Tan, Penang (MY); Saiful Bahari Saidan, Amapang (MY); Sze Yin Lee, Penang (MY)

(73) Assignee: Avago Technologies Imaging IP (Singapore) Pte.Ltd, Singapore (SG)

( * ) Notice: Subject to any disclaimer, the term of this patent is extended or adjusted under 35 U.S.C. 154(b) by 200 days.

(21) Appl. No.: 11/102,411

(22) Filed: Apr. 8, 2005

(65) Prior Publication Data

US 2006/0226379 A1    Oct. 12, 2006

(51) Int. Cl.
*G01N 21/86* (2006.01)

(52) U.S. Cl. .................... 250/559.4; 250/221

(58) Field of Classification Search ............. 250/559.4, 250/221, 235, 577, 208.1; 347/23, 106
See application file for complete search history.

(56) References Cited

U.S. PATENT DOCUMENTS 5,925,889 A * 7/1999 Guillory et al. ....... 250/559.16
6,561,641 B1   5/2003 Walker et al.

* cited by examiner

*Primary Examiner*—Que T. Le

(57) ABSTRACT

Media type is detected. A light beam is produced. The intensity of a specular reflectance component of the light beam is detected. The specular reflectance component results from the light beam being reflected off media. An indication of detected intensity of the specular reflectance component is compared to a mapping to determine media type of the media. The mapping maps detected intensity of the specular reflectance component to media type. The mapping uses only the detected intensity of the specular reflectance component, and no other components of light, to map detected intensity of the specular reflectance component to media type.

15 Claims, 2 Drawing Sheets

MEDIA RECOGNITION USING A SINGLE LIGHT DETECTOR

BACKGROUND

When printing with certain types of printers, such as ink jet printers, the type of media can have an effect on print quality. For example, while minimum ink migration may occur when printing on glossy photographic paper, a higher degree of migration will occur when printing on plain paper. Optimizing print on different color media may require different ink mixing. For this reason, many printers control ink volumes and other print characteristics based on media type.

Various media recognition mechanisms have been utilized. For example, many printers allow a user to indicate media type. Based on the media type information provided by the user, the printer can vary print characteristics.

Alternatively, an automated media detection system can be used. For example, a media detect sensor can be used to read an invisible-ink code pre-printed on the media.

Another type of automated media detection system uses a transmitter and two receptors at differing angles with respect to the surface of the media. The two sensors are used to measure, respectively, the specular reflectance of the media and the diffuse reflectance of the media. The ratio of these two reflectance values are analyzed to identify specific media type. Alternatively, a Fourier transform of the to reflective values is used to generate a spatial frequency signature for media. See, for example, U.S. Pat. No. 6,561,643 B1 issued to Walker et al. for Advanced Media Determination System for Inkjet Printing.

SUMMARY OF THE INVENTION

In accordance with an embodiment of the present invention, media type is detected. A light beam is produced. The intensity of a specular reflectance component of the light beam is detected. The specular reflectance component results from the light beam being reflected off media. An indication of detected intensity of the specular reflectance component is compared to a mapping to determine media type of the media. The mapping maps detected intensity of the specular reflectance component to media type. The mapping uses only the detected intensity of the specular reflectance component, and no other components of light, to map detected intensity of the specular reflectance component to media type.

DESCRIPTION OF THE EMBODIMENT

Figure 1:
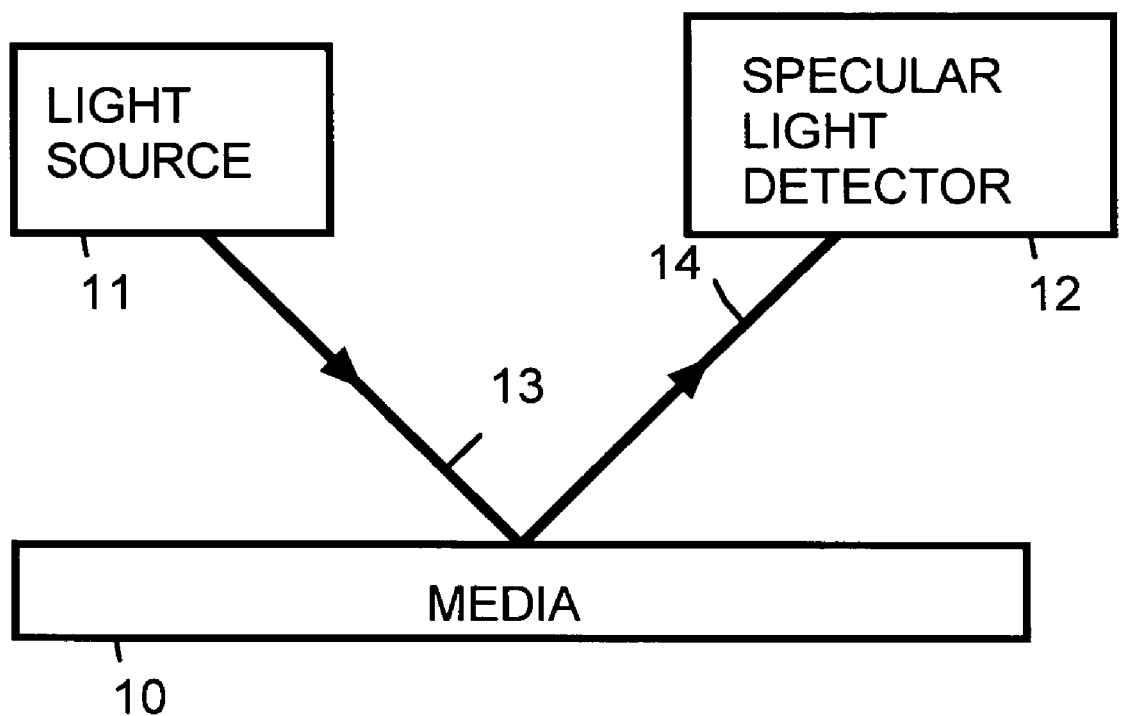
FIG. 1 is a simplified diagram that shows a media recognition system that uses a light source and a single light detector in accordance with an embodiment of the present invention.

FIG. 1 shows a media recognition system that includes a light source 11 and a single light detector 12. For example, the media recognition system is within a system that performs printing, such as a stand-alone printer, a multifunction device, a facsimile machine, or a copier or the media recognition system is within any other device where it is desirable to detect media type and/or presence.

Light source 11 generates a light beam, represented by arrow 13. The light beam is reflected by media 10. A specular reflectance component 14 of the light beam is detected by specular light detector 12. Specular reflectance component 14 is that portion of the light beam that reflects off media 10 at an angle equal to the angle of incidence at which the light beam struck media 10. In addition to producing specular reflectance component 14, when the light beam strikes media 10 some of the light is absorbed by media 10 and some is scattered off the surface of media 10 at angles not equal to the angle of incidence.

Light source 11 is, for example, a light-emitting diode (LED), such as, for example, a blue LED or a blue-violet LED. Alternatively, light source is any other light-emitting device capable of producing specular light reflected from media. Specular light detector 12 is, for example, a photo diode or some other device capable of detecting light intensity.

Figure 2:
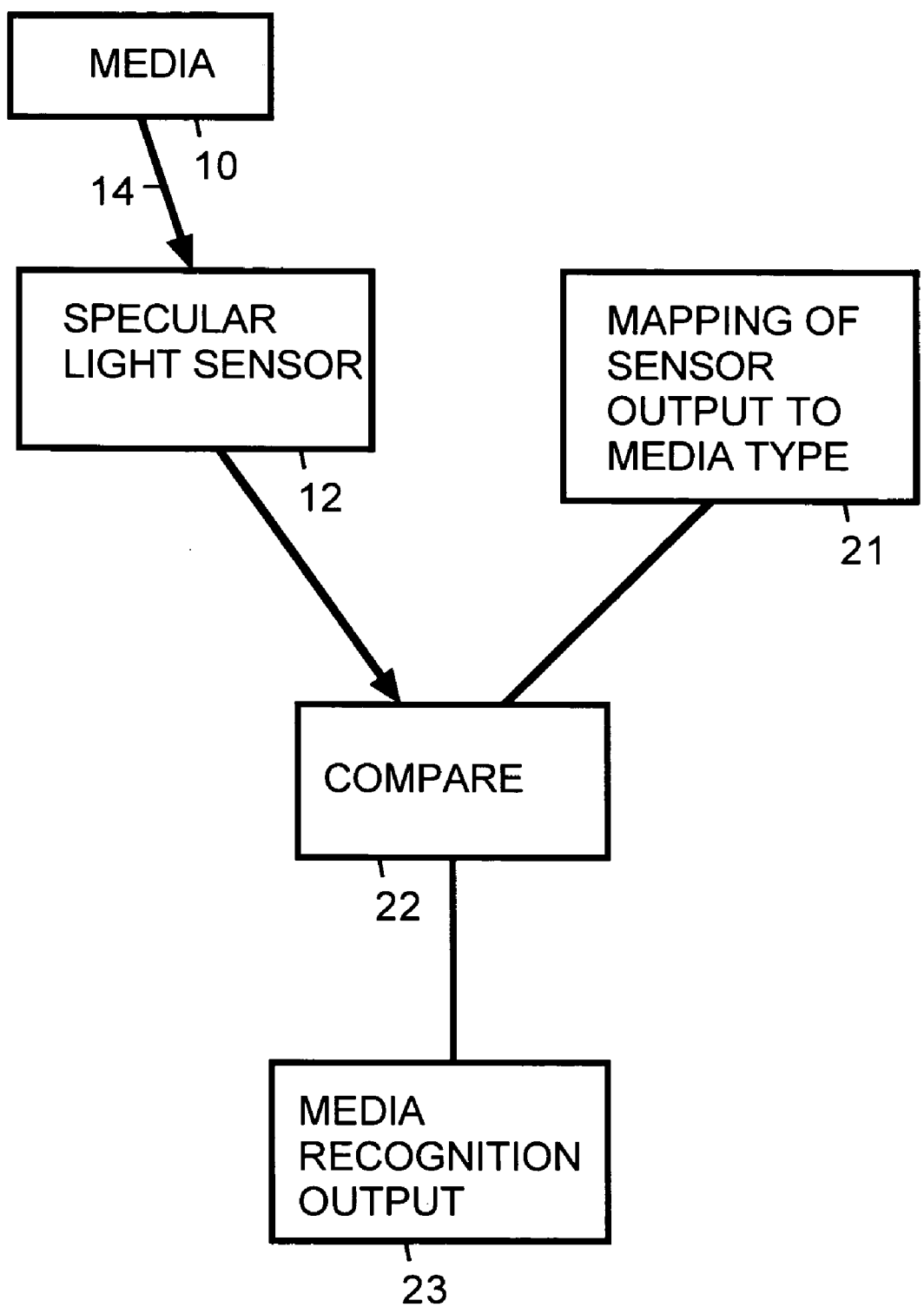
FIG. 2 illustrates operation of the media recognition system shown in FIG. 1 in accordance with an embodiment of the present invention.

FIG. 2 shows logical operation of the media recognition system shown in FIG. 1. After detecting specular reflectance component 14, specular light detector 12 forwards to a compare component 22 an indication of the intensity of light within specular reflectance component 14. The indication of the intensity of light within specular reflectance component 14 varies based on the reflectivity of media 10.

For example, specular light detector 12 includes an analog-to-digital converter and the indication of the intensity of light within specular reflectance component 14 is a digital indicator of intensity level. Alternatively, specular light detector 12 does not include an analog-to-digital converter and the indication of the intensity of light within specular reflectance component 14 is an analog indicator of intensity level.

Compare component 22 receives the indicator of the intensity of light and compares the indicator of the intensity of light with a mapping 22 of sensor output to media type to produce a media recognition output 23. For example, media recognition output 23 indicates a media type or indicates that there is no media detected.

For example, if the indication of the intensity of light within specular reflectance component 14 is an analog indicator of intensity, compare component 22 performs an analog-to-digital conversion before making the comparison. The mapping 22 of sensor output to media type can vary depending, for example, upon system configuration and expected media types.

Table 1 below shows an example mapping where expected media type includes blank transparency, blank white paper, blank plain paper, cyan colored plain paper, magenta colored plain paper, yellow colored plain paper and black colored plain paper:

TABLE 1

| Light Intensity | Media Type |
| --- | --- |
| 0–1 | No Media detected |
| 2 | Black colored plain paper |
| 3 | Yellow colored plain paper |
| 4 | Magenta colored plain paper |
| 5 | Cyan colored plain paper |
| 6 | Blank plain paper |
| 7 | Blank white paper |
| 8 | Blank transparency |

Table 1 can be derived for the media recognition system, for example, empirically by measuring light intensity for each expected media type and recording the result in mapping 22 of sensor output to media type.

The present invention allows detection of media types and the presence of media types using a single photo detector. The use of only a single photo detector results in a reduced material cost, a reduced process cost and reduced system complexity when implementing a media recognition system.

The forgoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

We claim:

1. A media recognition system comprising:
   a light source that produces a light beam;
   a light detector configured to detect intensity of a specular reflectance component of the light beam after the light beam is reflected off media, the light detector producing an indication of detected intensity of the specular reflectance component;
   a mapping that maps detected intensity of the specular reflectance component to media type, the mapping using only the detected intensity of the specular reflectance component, and no other components of light, to map detected intensity of the specular reflectance component to media type; and,
   a comparison component that compares the indication of detected intensity of the specular reflectance component to the mapping to determine media type of the media.

2. A media recognition system as in claim 1 wherein the light source is a light-emitting diode.

3. A media recognition system as in claim 1 wherein the light source is one of the following:
   a blue light-emitting diode;
   a blue-violet light-emitting diode.

4. A media recognition system as in claim 1 wherein the light detector is a photo diode.

5. A media recognition system as in claim 1 wherein the mapping includes a detected intensity of the specular reflectance component that indicates no media is present.

6. A method for detecting media type comprising:
   producing a light beam;
   detecting intensity of a specular reflectance component of the light beam after the light beam is reflected off media; and,
   comparing an indication of detected intensity of the specular reflectance component to a mapping to determine media type of the media, wherein the mapping maps detected intensity of the specular reflectance component to media type, the mapping using only the detected intensity of the specular reflectance component, and no other components of light, to map detected intensity of the specular reflectance component to media type.

7. A method as in claim 6 wherein the light beam is produced using a light-emitting diode.

8. A method as in claim 6 wherein the light beam is produced using one of the following:
   a blue light-emitting diode;
   a blue-violet light-emitting diode.

9. A method as in claim 6 wherein the intensity of a specular reflectance component of the light beam is detected using a photo diode.

10. A method as in claim 6 wherein the mapping includes a detected intensity of the specular reflectance component that indicates no media is present.

11. A device that detects media type comprising:
    means for producing a light beam;
    means for detecting intensity of a specular reflectance component of the light beam after the light beam is reflected off media; and,
    means for comparing an indication of detected intensity of the specular reflectance component to a mapping to determine media type of the media, wherein the mapping maps detected intensity of the specular reflectance component to media type, the mapping using only the detected intensity of the specular reflectance component, and no other components of light, to map detected intensity of the specular reflectance component to media type.

12. A device as in claim 11 wherein the light beam is produced using a light-emitting diode.

13. A device as in claim 11 wherein the light beam is produced using one of the following:
    a blue light-emitting diode;
    a blue-violet light-emitting diode.

14. A device as in claim 11 wherein the intensity of a specular reflectance component of the light beam is detected using a photo diode.

15. A device as in claim 11 wherein the mapping includes a detected intensity of the specular reflectance component that indicates no media is present.

* * * * *